United States Patent
Mendes et al.

[11] Patent Number: 5,259,380
[45] Date of Patent: Nov. 9, 1993

[54] LIGHT THERAPY SYSTEM

[75] Inventors: Emanuel Mendes, Petach Tikva; Yonatan Lison, Tel-Aviv, both of Israel

[73] Assignee: Amcor Electronics, Ltd., Tel Aviv, Israel

[21] Appl. No.: 615,050

[22] Filed: Nov. 15, 1990

[30] Foreign Application Priority Data

Nov. 4, 1987 [IL] Israel ........................ 84376
Aug. 8, 1988 [GB] United Kingdom ........... 88188099

[51] Int. Cl.⁵ .......................... A61N 5/06; H05B 33/00
[52] U.S. Cl. .......................... 607/115; 606/2; 606/3; 606/9
[58] Field of Search .......... 128/395, 396, 397; 606/2, 3, 9

[56] References Cited

U.S. PATENT DOCUMENTS

| | | | |
|---|---|---|---|
| 3,659,613 | 5/1972 | Bredemeier | 128/395 |
| 3,785,383 | 1/1974 | Dotto | 128/414 |
| 4,112,923 | 9/1978 | Tomecek | 128/395 |
| 4,232,678 | 11/1980 | Skovajsa | 128/395 |
| 4,324,250 | 4/1982 | Braun et al. | 128/395 |
| 4,535,784 | 8/1985 | Rohlicek et al. | |
| 4,553,546 | 11/1985 | Javelle | 128/395 |
| 4,583,526 | 4/1986 | Ali | 128/6 |
| 4,600,011 | 7/1986 | Watmough | 128/664 |
| 4,601,037 | 7/1986 | McDonald | 128/395 |
| 4,646,743 | 3/1987 | Parris | 128/396 |
| 4,671,285 | 6/1987 | Walker | 128/395 |
| 4,686,986 | 8/1987 | Fenyo et al. | 128/396 |
| 4,796,967 | 1/1989 | Mori | 350/96.10 |
| 4,839,513 | 6/1989 | Wijtsma | 250/504 R |
| 4,898,439 | 2/1990 | Mori | 128/397 |
| 4,905,690 | 3/1990 | Ohshiro et al. | 128/395 |
| 4,909,254 | 3/1990 | Wilkinson | 128/396 |
| 4,930,504 | 6/1990 | Diamantopoulos et al. | 128/395 |

FOREIGN PATENT DOCUMENTS

| | | | |
|---|---|---|---|
| 0324490 | 7/1989 | European Pat. Off. | 128/395 |
| 616556 | 7/1935 | Fed. Rep. of Germany | 128/396 |
| 3401492 | 7/1985 | Fed. Rep. of Germany | 128/395 |
| 0651477 | 9/1985 | Switzerland | 128/395 |
| 1266540 | 10/1986 | U.S.S.R. | 128/395 |
| 818688 | 8/1959 | United Kingdom | 128/395 |
| 2212010 | 7/1989 | United Kingdom | 128/395 |

Primary Examiner—Jessica J. Harrison, Jr.
Attorney, Agent, or Firm—Natter & Natter

[57] ABSTRACT

A light therapy system utilizes an array of light emitting diodes which emit noncoherent light in a narrow bandwidth centered at a designated wave length. The diodes are mounted to project and focus their output on a dermal zone of a patient. A continuous or a pulsed voltage differential is utilized to energize the diodes. Higher voltage differential and peak current flow across the diodes is provided in pulsed operation than in continuous operation. With a designated wave length in the infra red bandwidth, a treatment regimen including a session of 5–10 minutes of continuous operation and a session of 5–10 minutes of pulsed operation once or twice per day has been effective in alleviating various musculoskeletal disorders. A similar treatment regimen utilizing diodes emitting light centered at the red light wave length has proven effective in the treatment of skin ulcers and delayed post operative wound healing.

30 Claims, 3 Drawing Sheets

LIGHT THERAPY SYSTEM

BACKGROUND OF THE INVENTION

1. Field of the Invention

This invention relates generally to light therapy and more particularly to a therapy system utilizing light emitting diodes as a source of biostimulative noncoherent radiation.

2. Related History

Monochromatic light radiation at defined wave lengths has produced beneficial biostimulative effects and has been known to trigger specific biological functions, such as, phototaxis, photorepair, cell division and photoperiodics clocks. Stimulation occurred, however, with light radiation in controlled wave lengths and only in conjunction with controlled administration dosages. Application of broad band light radiation, overdosage, or inadequate dosage, did not provide the beneficial biostimulative effects.

While the exact mechanism by which the beneficial biostimulative effects have been achieved is not precisely known, several theories have been propounded. It has been suggested that monochromatic light radiation penetrated body tissue and was absorbed, reflected and scattered to excite molecules within damaged tissue to thereby accelerate repair.

A further theory suggested that different cells had different photoreceptors which responded to only particular wave lengths of light radiation. This theory supported the phenomenon that the application of only certain wave lengths of light radiation resulted in biostimulative effects. It was known that the application of too much light power did not produce biostimulative effects; this was possibly due to the destruction of the photoreceptors, while inadequate dosage resulted in the inability to trigger the photoreceptors.

Light therapy has utilized lasers with relatively low power and biostimulative treatment utilizing lasers has been referred to as "soft" laser therapy. In such applications, low level laser energy radiation has been successfully employed to stimulate wound healing and treat inflammatory conditions. In recent years, soft laser therapy has been successfully employed for the treatment of musculoskeletal disorders and skin ulcers. Both low level helium neon lasers and infra red lasers have been employed to generate radiation characterized by monochromacity and coherency. Soft radiation therapy utilizing helium neon lasers necessitated equipment which was relatively large and highly expensive and often required cooling systems. Such lasers were utilized to provide a continuous, relatively low power, e.g. in the range of 10 MW, beam of coherent radiation having sharply defined wave length which remained stable to within plus or minus 1 nm.

Infra red laser therapy utilized a laser system to generate a coherent beam of monochromatic sharply defined radiation in the infra red wave length band. The lasing medium utilized semiconductor diode. The output from the laser diode was a sharply diverted and conical and was difficult to couple efficiently to an optical system. Because of its coherency, it required diffraction limited collection, focusing and coupling optics which added significantly to the cost of the resulting system.

Laser diodes required higher operating currents than conventional light emitting diodes in order to maintain adequate population inversion by producing a high density of electron hole pairs. The resulting radiation was essentially monochromatic and coherent whereas the radiation of a conventional light emitting diode is noncoherent and encompasses a broader spectral bandwidth. Because of the relatively high current density through a laser diode, laser diodes could only be operated in a pulsed mode wherein the current sufficient to cause population inversion was passed through the diode as a pulse train comprising pulses of very short duration, e.g. in the order of nanoseconds. As a result, laser diode switching frequency was required to be extremely fast which necessitated complex and expensive power supplies.

Laser diodes did possess advantages over helium neon lasers for use in soft laser therapy, in part due to the fact that the physical system was less expensive than that of helium neon lasers. In addition, laser diode systems were relatively small in size as compared with helium neon lasers of equivalent power rating. Laser diodes to date have been available in the infra red frequency range.

It has been previously theorized that the properties of laser radiation which resulted in the beneficial biostimulative effects of soft laser therapy were the monochromacity and coherence of laser radiation.

There appeared to be a need for the beneficial effects of the continuous operating characteristics provided by helium neon lasers to be combined with the lower cost and higher output power of laser diode systems.

It occurred to applicants that if biostimulative light radiation effects of soft laser therapy were not predicated upon absolute monochromacity and coherency of the radiation and that radiation within a defined bandwidth range could result in biostimulation, conventional light emitting diodes could be utilized.

SUMMARY OF THE INVENTION

In compendium, the present invention comprises a system for light therapy which utilizes noncoherent light generated by an array of conventional light emitting diodes with the radiation confined within a relatively narrow bandwidth of plus or minus 25 nm. The diode array is configured in a matrix to directly focus the light radiation on a reasonably sharply defined area of a patient without utilizing an optical system.

The diode array includes a plurality of diode banks connected in parallel with the diodes of each bank being series connected. By employing a large number of diodes, a relatively high power light radiation source is provided. The wave length of the light radiation emitted is a function of the particular light emitting diodes employed and may be selected from, for example, the red or infra red bandwidth range to correspond to radiation of conventional helium neon or infra red lasers without the necessity of changing the diode mounting configuration in the matrix. Alternate intermediate bandwidths may be selected by employing different diodes.

The diode array is powered by a switchable power supply source to selectively provide either a continuous or pulsed operation of the diode banks. A d.c. voltage rectifier and a control circuit are employed for providing a voltage of predetermined magnitude to a high voltage rail common with the diode banks in a continuous mode of operation.

In a pulsed mode, a voltage doubler rectifier and the control circuit provide a higher voltage differential across the diode banks in a pulse stream. The control circuit operates as a function of the output of a monolithic timer, the frequency and duty cycle of which are accurately controlled to generate a pulse chain which is applied to an analog switch. The output of the analog switch is received at operational comparators of a driver circuit and the comparators trigger power Darlingtons which are series connected in the diode banks.

A treatment regimen with red light radiation of 5-10 minutes of continuous and 5-10 minutes pulsed radiation once or twice per day was found effective in healing skin ulcers and post operative wounds. A treatment regimen with infra red radiation of 5-10 minutes continuous and 5-10 minutes pulsed radiation once or twice per day was found effective in treatment of facet joint osteoarthritis, degenerative knee disease, rheumatoid arthritis, chondromalacia patella and chronic tendonitis.

From the foregoing, it should be appreciated that it is an aspect of the present invention to provide a light therapy system of the general character described which is not subject to the disadvantages of the related history aforementioned.

To provide a light therapy system of the general character described suitable for soft laser therapy and having both the continuous operating characteristics of helium neon lasers and the high power pulsed output of laser diodes in a single unit is another aspect of the present invention.

A feature of the present invention is to provide a light therapy system of the general character described which is relatively low in cost.

A consideration of the present invention is to provide a light therapy system of the general character described which is lightweight and portable.

To provide a light therapy system of the general character described which is well suited for relatively low cost mass production fabrication is a still further consideration of the present invention.

Another aspect of the present invention is to provide a light therapy system of the general character described which produces therapeutic biostimulative effects in alleviating and healing a wide variety of ailments by employing noncoherent light radiation generated by a plurality of conventional light emitting diodes.

A still further consideration of the present invention is to provide a light radiation treatment method of the general character described whereby noncoherent radiation within a defined bandwidth range of plus or minus 25 nm is employed for biostimulation.

A further aspect of the present invention is to provide a light therapy method of the general character described which utilizes noncoherent radiation emanating from conventional light emitting diodes for the treatment of tendinitis, facet joint arthritis, chondromalacia patellae, degenerative knee disease, skin ulcers and for the promotion of post operative healing.

With these ends in view, the invention finds embodiment in certain combinations of elements, arrangements of parts and series of steps by which the aspects, features and considerations aforementioned and certain other aspects, features and considerations are hereinafter attained, all as fully described with reference to the accompanying drawings and the scope of which is more particularly pointed out and indicated in the appended claims.

BRIEF DESCRIPTION OF THE DRAWINGS

In the accompanying drawings in which is shown some of the various possible exemplary embodiments of the invention

DESCRIPTION OF THE PREFERRED EMBODIMENT

Referring now in detail to the drawings, the reference numeral 10 denotes generally a light therapy system constructed in accordance with and embodying the invention. The system 10 includes an array of light emitting diodes 12 which, in accordance with the present invention, comprise parallel banks of series connected conventional light emitting diodes configured to emanate light radiation within a narrow bandwidth of plus or minus 25 nm centered about a predesignated wave length. The selected wave length for red light radiation therapy is 660 nm while the selected wave length for infra red light radiation therapy is 940 nm. Other predesignated other wavelengths, for example 880 nm may be selected.

Figure 1:
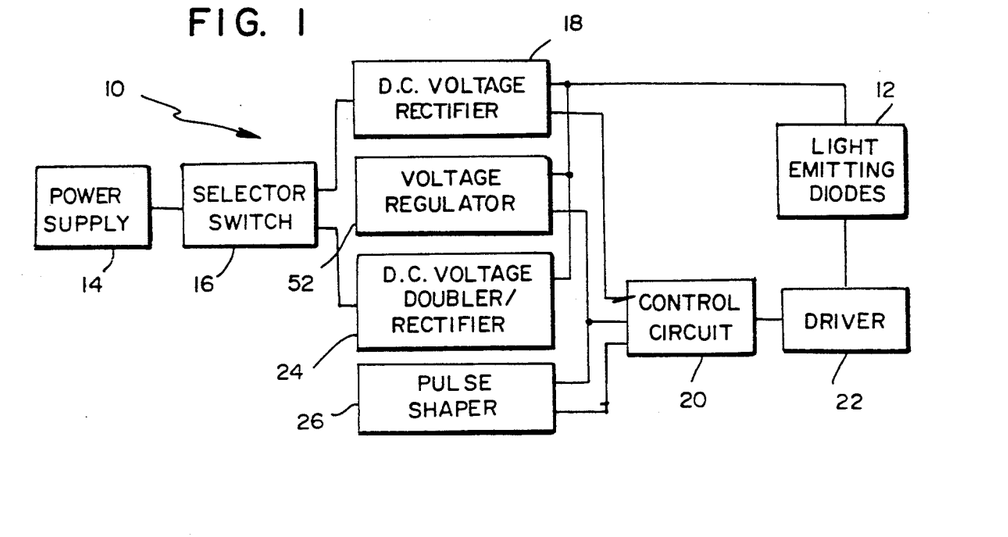
FIG. 1 is a schematized block diagram illustrating the functional components of a light therapy system constructed in accordance with and embodying the invention and showing a power supply, a selector switch, a pair of d.c. voltage rectifiers, a pulse shaper, a control circuit, a driver and a radiation source.

With reference to the schematized block diagram of FIG. 1, it will be seen that the diodes are energized through a suitable power supply 14 which may comprise an a.c. adaptor interconnected to the electrical mains and having an output of approximately 12 volts a.c. The output of the adaptor is received at a selector switch 16 which may comprise a single pole triple throw switch with one of the switch positions being off, the other position being continuous operating mode and the last position being pulsed operating mode.

In the continuous mode of operation, the selector switch interconnects the power supply with a voltage rectifier circuit 18, the output +V of which is fed to a common high voltage rail of banks of light emitting diodes 12. In addition, an output of the voltage rectifier 18 is also fed to a control circuit 20 which includes an analog switch 25 and from the control circuit 20 to a driver circuit 22. Actuation of the driver circuit 22 serves to complete a path for current flow through the banks of light emitting diodes 12.

With the selector switch 16 placed in the pulsed mode of operation, the output of the power supply 14 is fed to a d.c. voltage doubler rectifier 24 having an output voltage +V higher than that of the rectifier 18. The higher output voltage of the voltage doubler rectifier 24 is fed to the common rail of the banks of light emitting diodes.

A pulse shaper 26 is utilized in the pulsed mode. The pulse shaper 26 may comprise a monolithic timing circuit, the free running frequency and duty cycle of which can be adjusted and controlled. The pulse shaper output 26 is transmitted to the control circuit 20 and the control circuit provides a pulsed output corresponding in frequency and duty cycle to the output of the pulse shaper 26. The control circuit output is transmitted to the driver circuit 22 and the driver circuit 22, in turn, controls current flow through the diodes 12 in accordance with the pulse shaper output.

Figure 2:
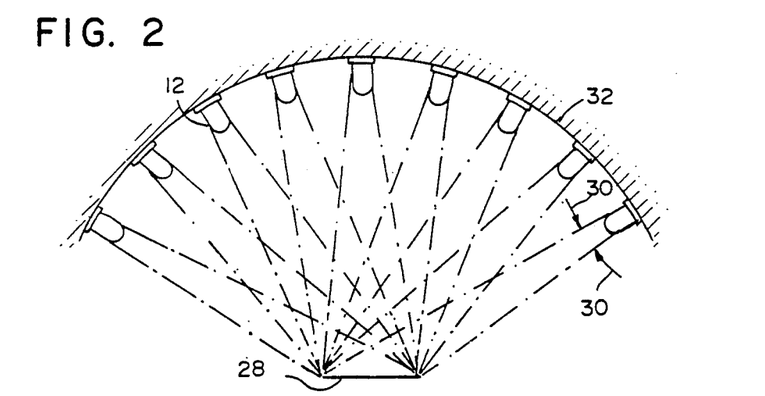
FIG. 2 is a schematized illustration of the manner in which light emitting diodes may be mounted to a convex dished base surface for focusing without an optical system.

FIG. 2 comprises a schematic illustration of a typical section through a convex spherical mounting base for the diodes 12. Focusing of the light output of an array of diodes without an optical system is an aspect of the invention. Preferably, the output of all of the light emitting diodes 12 is directed to a central focal point without lenses, mirrors or other optical systems. The area of focus of the light emitting diodes comprises a planar zone 28 of approximately 2 cm$^2$ in area, at a focal length of approximately 3 cm. When employing red light emitting diodes, the light power density, in continuous wave mode, is 15 mw/cm$^2$ as compared with the light power density of the sun at noon at 60 mw/cm$^2$.

In the pulsed mode of operation, with a pulse shaper 26 generating an output signal at 100 Hz and a typical duty ratio of 10%, the peak light power at focus, for the red light emitting diodes is 75 mw and the average light power is 7.5 mw.

When configured as an infra red radiation emitter and with infra red radiating light emitting diodes having a wave length of 940 nm+25 nm and a focus beam area of 2 cm$^2$, typical light power at focus in the continuous wave mode light radiation intensity is 25 mw and maximum light power density is 20 mw/cm$^2$. In the pulsed mode, the pulse shaper 26 is configured to provide an output signal of 100 Hz with a typical duty cycle of 1%, the peak power at focus is 270 mw and the average light power at focus is 2.7 mw. It should be understood that the foregoing light power specifications are merely exemplary and it is believed that diode banks having higher light power will provide therapeutic biostimulative effects.

The light emitting diodes 12 are preferably selected with an angle of beam divergence of 12 degrees, indicated within the arrows 30 illustrated in FIG. 2. A narrower angle of divergence, e.g. 8 degrees, will provide more concentrated light power at the focal point.

As illustrated in FIG. 2, the diodes 12 are each mounted within a concave spherical base 32 in a position to focus the light radiation on the planar focal zone 28 of approximately 2 cm$^2$. If, for example, 15 diodes are employed, they can be dispersed about the base 32 in concentric circular arrays of, for example, 9 diodes within a larger diameter circle and 6 diodes within a concentric circle of smaller diameter, with each of the diodes being directed toward a focal point at the center of the planar focal zone 28.

Figure 3:
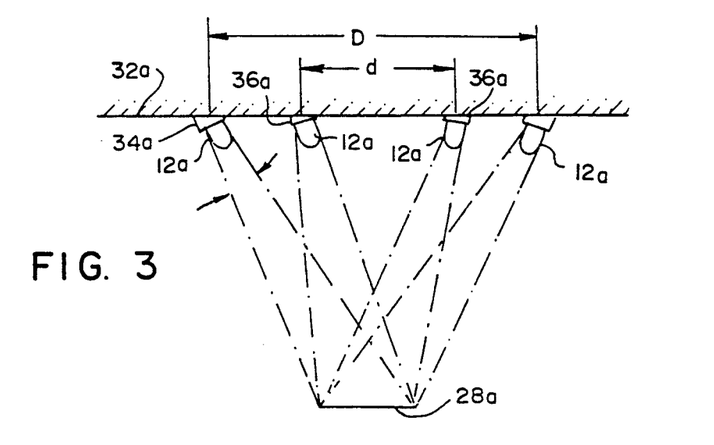
FIG. 3 is a schematized illustration of an alternate manner in which light emitting diodes may be mounted to a planar surface for focusing without an optical system.

In FIG. 3, an alternate embodiment of the diode mounting and focusing pursuant to the invention is illustrated. In this embodiment, like numerals have been employed to denote like components, however, bearing the suffix "a". A plurality of diodes 12a are mounted in pairs of concentric circles to a planar base 32a. The diodes are positioned within one of two concentric circles, the smaller circle being defined by a diameter "d" and a larger circle being defined by a diameter "D". The smaller circle may include, for example, 6 diodes 12a and the larger circle may include, for example, 12 diodes. Each diode 12a includes an angular mount directing the center of the light beam projecting from the diode to a focal point with a focal length, from the planar support base 32a, of 31 mm. Accordingly, 12 angular mounts 34a within the larger circle are preferably inclined at an angle of convergence of, for example, 61° while 6 angular mounts 36a positioned within the smaller circle are at an angle of convergence of, for example, 74°.

Figure 4:
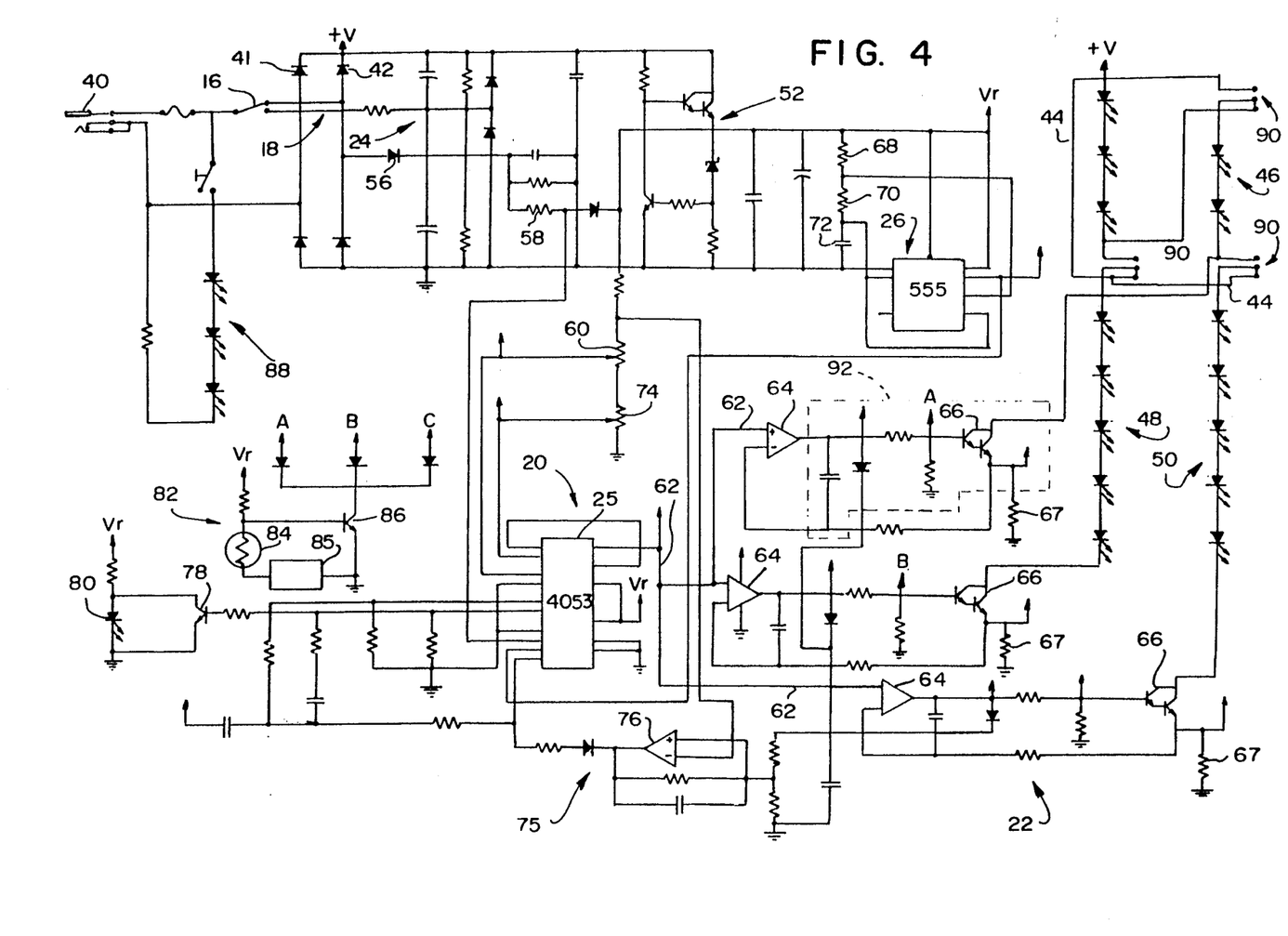
FIG. 4 comprises a circuit diagram, with portions deleted for clarity, employing the components functionally depicted in FIG. 1 in a typical exemplary configuration.

Referring now in detail to FIG. 4 wherein a typical circuit is illustrated for a light therapy system 10 constructed in accordance with the invention, from the power supply 14, an a.c. power supply voltage of approximately 12 volts is received through a power jack 40. With the selector switch 16 in the continuous mode position, one leg of the power supply is fed through a diode 41 and the other leg through a diode 42 of the voltage rectifier 18. A rectified d.c. output +V is provided.

The output +V appears along a common rail 44 of three banks 46, 48, 50 of light emitting diodes 12, with the diodes of each bank being interconnected in series when the circuit is in a configuration for powering light radiation in the red wave length. The opposite (low voltage) ends of each of the banks 46, 48, 50 are connected to a low voltage drain such as a resistor 67 coupled to ground through the driver circuit 22.

The control circuit 20 is utilized to actuate the driver circuit 22 and may comprise a 4053 analog switch 25. For purposes of operating the analog switch 25, a fixed regulated voltage Vr is generated at a voltage regulator section 52 and is applied to pins 4 and 16 of the analog switch 25. The voltage Vr remains constant regardless of the value of +V, provided +V is above Vr.

In the continuous operating mode of the selector switch 16, the analog switch 25 receives a high signal through the selector switch 16, a diode 56 and a resistor 58 with the signal applied at pin 11 of the analog switch 25. In the pulse mode, the signal at pin 11 is low.

Additionally, in the continuous mode of operation, the regulated voltage Vr, adjusted at a potentiometer 74, is applied to pin 13 of the analog switch 25 and is employed to set the level of current flow through the diode banks. The output signal of the analog switch appears at pin 14 and is a constant signal of the same value as applied to pin 13.

The output signal appearing at pin 14 is fed through a line 62 to the driver 22. The driver 22 includes, for each of the banks, 46, 48, 50, a comparator 64, e.g. LM 324, which receives the analog switch output signal having a value as adjusted by the potentiometer 74. Each comparator 64, in turn, switches to trigger a power Darlington 66. When the power Darlington closes, current flows through its associated diode bank and through a sampling resistor 67, one end of which is connected to a second input of the comparator 64 to provide a closed loop current sampler and switch the Darlington in the event of excessive current flow. Thus, the level of current flow through each of the diode banks is controlled as a function of the potentiometer 74 in the continuous mode.

In the pulsed mode of operation, the selector switch 16 is in its lower position and the signal at the analog switch pin 11 is low. The power supply is connected to a voltage doubler 24 in lieu of the diode 42 to provide an output d.c. voltage +V which is higher than that generated by the rectifier circuit 18 in the constant mode.

As a result of the signal on pin 11 of the analog switch 25 going low, the output of the analog switch now becomes a function of the signals on pins 10 and 2. Pin 10 receives an input generated by the pulse shaper 26. The pulse shaper 26 may comprise a 555 integrated timer circuit.

The frequency and duty cycle of the pulse shaper 26 are controlled by a pair of resistors 68, 70 and a capacitor 72 which may have preset values for a particular application or which may be variable.

The level of current through the diode banks is set by the regulated voltage adjusted at a potentiometer 60 and applied at pin 2 of the analog switch 25. The output of the analog switch 25 appearing at pin 14, hence the signal on the line 62, is a pulse chain which is representative of the frequency and duty cycle of the pulse shaper 26 and having an amplitude value as adjusted by the potentiometer 60. The pulse chain signal switches the comparators 64 which in turn switch the power Darlingtons 66 of the driver 22 to provide a pulse flow of current through the banks 46, 48 and 50 of diodes 12 with the level of current being a function of the setting of the potentiometer 60.

A test circuit 75 is provided for the purpose of detecting faults in the driver circuit 22. The test circuit 75 includes a comparator 76 e.g. LM 324, which receives, as one input, a voltage derived from the regulated voltage Vr, and, as its other input, a signal which is the function of the outputs of the comparators 64. In the event of a fault in the circuitry of the diode banks, such as, for an example, an open circuit in one of the diodes, insufficient supply voltage or similar fault in the drive circuitry, a high level signal will result. Such high level signal causes the test circuit comparator 76 to have a high output signal which, in turn, appears at input pin 9 of the analog switch 25. This signal results in the analog switch 25 and its associated circuitry generating a low frequency, e.g. 2 Hz signal at an output pin 3 which, in turn, appears at the base of a transistor 78 and causes the transistor to switch, resulting in a low frequency flash rate at a light emitting diode 80.

The invention also includes a timer and high temperature safety shut off circuit 82 which includes a thermistor 84 and a timer 85. The timer 85 opens when a predetermined or adjustably set radiation treatment time has lapsed, and the thermistor 84 opens in the event of excessive temperatures. When the thermistor 84 or timer 85 opens, a triggering potential is applied to the base of a transistor 86. The transistor 86 is connected to the base of each of the power Darlingtons. As a result, when the transistor 86 closes, the signal at the base of the power Darlingtons becomes low and the power Darlingtons will not permit current flow through the diode banks. Alternately an external timer may be associated with the power supply 14.

It should be noted that the circuit depicted in FIG. 4 is illustrated in a configuration for the utilization of visible red wave length light emitting diodes in the diode banks 46, 48, 50. In the event infra red light emitting diodes are utilized, a plurality of visible red wave length light emitting diodes 88 are interconnected in the circuit for the purpose of enabling the focusing of the infra red radiation upon the affected area for treatment.

In addition, it has been found that when utilizing infra red wave length light emitting diodes, it is preferable to array the diodes in two banks rather than three banks. Accordingly, circuit jumpers 90 are provided to configure the diode banks for optional utilization of the same basic circuit in either configuration. Thus, when utilizing infra red wave length light emitting diodes, the jumpers 90 are interconnected between the uppermost and the middle terminals rather than as illustrated in FIG. 4. As a result, the power Darlington and its associated circuit depicted within a dashed block 92 is not utilized.

The efficacy of light radiation treatment utilizing red and infra red radiation generated by light emitting diodes in accordance with the present invention has been established in recent clinical studies. A double-blind clinical trial was conducted utilizing 432 patients with musculo-skeletal disorders, skin ulcers, post-operative delayed wound healing and chronic pain. The patients were divided into three groups, one of which was treated with light emitting diode generated radiation in the red wave length, i.e. 660 nm±25 nm, the other of which was treated with light emitting diode generated infra red wave length radiation, i.e. 940 nm±25 nm and the third of which was treated with a placebo device.

The protocol was designed to test the assumption that light radiation treatment in accordance with the invention is clinically safe and effective. In order to test efficacy, it was necessary to identify and control all variables which could influence the healing rate and pain relief. Accordingly, the protocol required the elimination of all other simultaneous physiotherapy or anti inflammatory drug treatment. Pain relief drugs however, were allowed and the decrease in dosage was considered an indicator of improvement.

The test was conducted with daily treatment of 10 minutes per day of combined pulse and continuous wave radiation transdermally administered.

Figure 5:
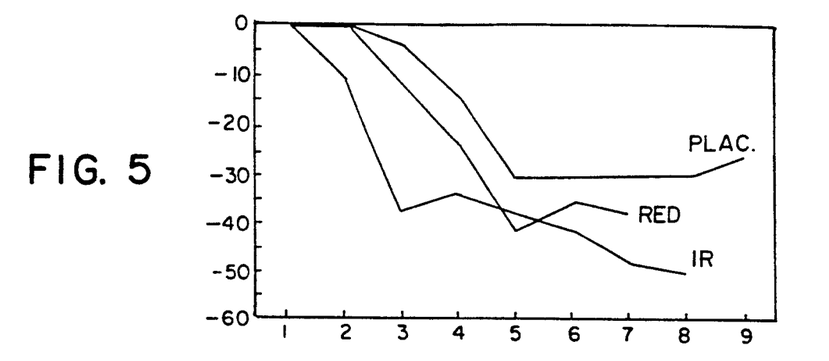
FIG. 5 is a graphic representation of the comparative degrees of relief of low back pain in patients with facet joint osteoarthritis over a course of treatments with infra red radiation and red radiation in accordance with the invention as compared with a placebo device.

With reference now to FIG. 5, wherein a comparison of the degree of pain relief (low back night pain) on patients with facet joint osteoarthritis is illustrated, the Y axis of the graph reflects change in percentage of degree of low back pain and the X axis represents days of treatment. The test clearly revealed that a significant improvement in pain was achieved within the first five days of treatment and that patients treated with infra red radiation in accordance with the invention showed a more significant improvement than those receiving other treatment.

Figure 6:
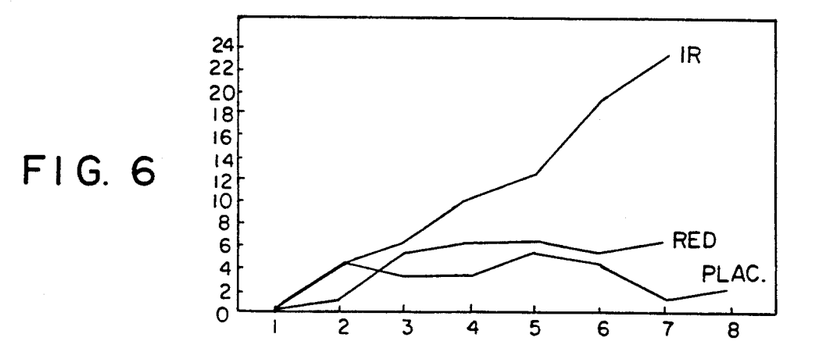
FIG. 6 is a graphic representation of the comparative ability of patients with degenerative knee disease to negotiate stairs over a course of treatments with infra red radiation and red radiation in accordance with the invention as compared with radiation from a placebo device.

FIG. 6 comprises a graph comparatively indicating the ability of patients with degenerative knee disease to ascend stairs. The Y axis of the graph is a measure of change in percentage while the X axis comprises days of treatment. It was noted that patients treated with infra red radiation in accordance with the invention illustrated a marked improvement in the ability to ascend stairs.

Figure 7:
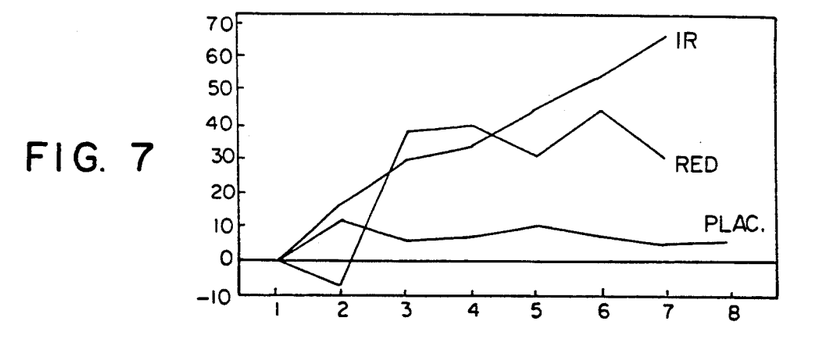
FIG. 7 is a graphic representation of walking time tolerance in patients with degenerative knee disease over a course of treatments with infra red radiation and red radiation in accordance with the invention as compared with a placebo device.

A comparison of walking time tolerance in patients with degenerative knee disease is illustrated in the graph of FIG. 7. The Y axis comprises the change in percentage while the X axis reflects days of treatment. It should be noted that patients treated with infra red radiation in accordance with the invention showed a significant improvement over those treated with red radiation and over those treated with the placebo.

Figure 8:
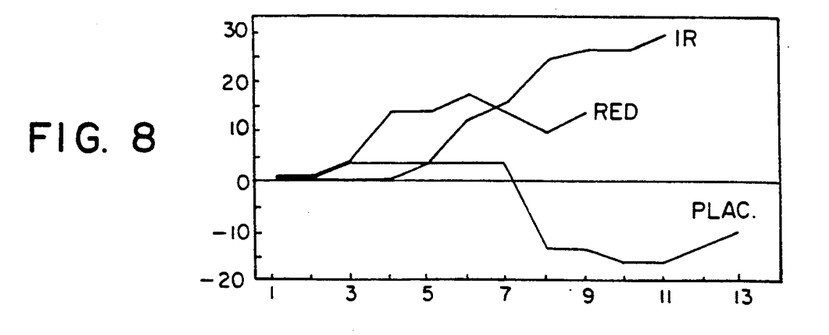
FIG. 8 is a graphic representation of the ability of patients with chondromalacia of the patella to negotiate stairs over a course of treatments with infra red radiation and red radiation in accordance with the invention as compared with a placebo device.

A comparison of the ability to descend stairs in patients suffering from chondromalacia patella is illustrated in the graph of FIG. 8. In this graph, the Y axis comprises the change in the percentage while the X axis reflects days of treatment. The results of the test reflected in this graph demonstrate that patients treated with infra red radiation in accordance with the invention illustrated a marked improvement in the ability to descend stairs with those receiving infra red radiation having a more significant improvement over those receiving red radiation and those being treated with the placebo.

With respect to the efficacy of radiation treatment in accordance with the present invention on the healing of skin ulcers and post operative wounds, the study indicated that patients treated with a placebo showed a 41% improvement, those treated with infra red radiation in accordance with the invention showed a 58% improvement and those treated with red light radiation in accordance with the invention illustrated an 89% improvement.

A recent clinical study was conducted on twenty one patients with thirty one post operative delayed healing open wounds which were resistant to conventional therapy. The patients were divided into three groups, one of which received red light radiation in accordance with the invention, the other group receiving infra red light radiation in accordance with the invention and the third group receiving a placebo treatment. The treatments comprised daily light treatments of 14 minutes combined, 7 minutes of continuous wave followed by 7 minutes of pulse wave radiation daily. Every ten days, accurate measurements of the wounds were performed. The results of the study indicated that of those patients receiving red light radiation, all patients improved, two healed completely and the total start area of all wounds was reduced to 11% after twenty days of treatment. With respect to the group receiving infra red radiation, one patient's condition worsened in one wound and showed no change in the other wounds, all other patients showed improvement and the total start area of all the wounds was reduced to 42%.

In the third group which received a placebo treatment, two patients' condition showed no change and the total start area of all wounds was reduced to 59%.

The efficacy of light radiation treatment utilizing conventional light emitting diodes in accordance with the present invention has been established.

Thus, it will be seen, that there is provided a light radiation therapy system which meets the various aspects, features and considerations of the present invention and which is well suited for practical use.

As various changes might be made in the invention as above set forth without departing from the spirit of the invention, it is to be understood that all matter herein described or shown in the accompanying drawings is to be interpreted as illustrative and not in a limiting sense.

Having thus described the invention, there is claimed as new and desired to be secured by Letters Patent:

1. A light therapy system comprising one plurality of light emitting diodes, each diode including means for emitting noncoherent light radiation, the noncoherent light radiation being in a narrow bandwidth centered at a designated wavelength, the designated wavelength being the same for all diodes of the plurality, the narrow bandwidth being in the order of 25 nm above and below the designated wavelength, means for concentrating the light radiation of the plurality of diodes and projecting the light radiation to a zone on an area, the zone being spaced from the diodes by a focal distance, and means for energizing the diodes, the means for energizing including means for providing a voltage differential across each of the diodes of the plurality of diodes the diodes being arrayed in a plurality of diode banks, the diodes of each diode bank being series connected, the means for providing a voltage differential including means for providing a voltage potential, a control circuit for controlling energy flow through the diodes, the control circuit including driver circuit means for coupling the diodes of each diode bank between the voltage potential and a voltage drain, the control circuit further including an analog switch, means for generating an adjusted regulated voltage, means operatively interconnecting the adjusted regulated voltage with one input of the analog switch, the analog switch receiving the adjusted regulated voltage and generating an output voltage potential which is a function of the adjusted regulated voltage, the driver circuit means including transistor switching means associated with each diode bank and series connected with each diode bank between the voltage potential and the voltage drain for controlling current flow through the diode bank, the drive circuit means further including an operational comparator associated with each transistor switching means, each operational comparator including a first input and a second input, the control circuit including means operatively interconnecting the analog switch output voltage potential with the first input of each operational comparator, each operational comparator generating an output, the transistor switching means including a base, means operatively interconnecting the output of each operational comparator with the base of its associated transistor switching means, each transistor switching means switching on to interconnect its associated diode bank between the voltage potential and the voltage drain to permit current flow through the diode bank when the output of its associated operational amplifier is high, the driver circuit means further includes means for monitoring current flow through each of the diode banks, the means for monitoring current flow including means operatively interconnecting the second input of each operational comparator with a location in the path of current flow between the voltage potential, the diode bank and the voltage drain, the voltage at the location being a function of current flow through the diode bank, whereby a voltage which is a function of the current flowing through each diode bank appears at the second input of the associated operational comparator, each operational comparator comparing the value of the voltage at the first input with the value of the voltage at the second input and generating a high output when the voltage at the first input is greater than the voltage at the second input, each operational comparator generating a low output when the voltage at the second input is greater than the voltage at the first input to thereby switch the transistor switching means off to limit excessive current flow through its associate diode bank.

2. A light therapy system as constructed in accordance with claim 1 wherein the plurality of diodes comprises in the order of ten to twenty diodes.

3. A light therapy system as constructed in accordance with claim 1 wherein the narrow bandwidth is centered at 660 nm, the light radiation being in a visible red wavelength band.

4. A light therapy system as constructed in accordance with claim 3 wherein the diodes are arrayed in two diode banks.

5. A light therapy system as constructed in accordance with claim 1 wherein the narrow bandwidth is centered at 940 nm, the light radiation being in an infra red wavelength band.

6. A light therapy system as constructed in accordance with claim 5 wherein the diodes are arrayed in three diode banks.

7. A light therapy system as constructed in accordance with claim 1 wherein the light radiation is projected with a light power density on the zone in the order of between 15 mw/cm$^2$ and 30 mw/cm$^2$.

8. A light therapy system as constructed in accordance with claim 1 wherein the light radiation is projected with an average light power at the zone in the order of 2 mw through 10 mw.

9. A light therapy system as constructed in accordance with claim 1 wherein the means for concentrating the light radiation comprises a base, means mounting each diode to the base and means for orienting the light radiation from each diode toward a center of the zone.

10. A light therapy system as constructed in accordance with claim 9 wherein the base is formed with a concave spherical contour, the means for orienting the light radiation from each diode comprising the concave spherical contour.

11. A light therapy system constructed in accordance with claim 1 further including pulse shaper means, the pulse shaper means comprising an integrated timer, means for fixing the frequency and duty cycle of the pulse shaper means, the pulse shaper means generating an output signal of a predetermined frequency and duty cycle, means operatively interconnecting the pulse shaper output signal with a further input of the analog switch, the analog switch receiving the adjusted regulated voltage and the pulse shaper output signal and in response thereto, generating an output which has a voltage potential which is a function of the adjusted regulated voltage and which is modulated as a function of the pulse shaper output signal, each operational comparator generating a high output and a low output as a function of the frequency and duty cycle of the pulse shaper output signal.

12. A light therapy system as constructed in accordance with claim 11 wherein the duty cycle ranges between 1% and 10%.

13. A light therapy system as constructed in accordance with claim 11 wherein the means for fixing the frequency and duty cycle of the pulse shaper means comprises a capacitor and at least one resistor and means operatively interconnecting the means for fixing with the integrated timer.

14. A light therapy system as constructed in accordance with claim 11 wherein the control circuit includes means for generating a second adjusted regulated voltage, the second adjusted regulated voltage being of a higher voltage potential than the adjusted regulated voltage, the analog switch including a mode selection input, the control circuit further including means for selecting between a constant light radiation emission mode or a pulsed light radiation emission mode, the control circuit further including means operatively interconnecting the means for selecting with the mode selection input, the analog switch monitoring the means for selecting through the mode selection input and in response to the selection of the constant light radiation emission mode, generating an output voltage which is a function of only the adjusted regulated voltage and in response to the selection of the pulsed light radiation emission mode, generating an output voltage which is a function of the second adjusted regulated voltage modulated as a function of the pulse shaper output signal, whereby higher current flow passes through each of the diodes when the pulsed light radiation emission mode is selected.

15. A light therapy system as constructed in accordance with claim 1 further including jumper means associated with the diode banks, the jumper means connecting the diodes of the diode banks to provide two diode banks in one configuration and to provide three diode banks in another configuration, whereby an optimal diode bank arrangement may be selected to be compatible with the designated wavelength of the diodes employed.

16. A light therapy system as constructed in accordance with claim 1 further including means for detecting faults in the driver circuit and for generating a signal indicative of a detected fault.

17. A method of treating musculoskelatal disorders in patents, the method comprising the steps of:
(a) providing a plurality of light emitting diodes which generate infra red light radiation only in a narrow bandwidth centered at approximately 940 nm,
(b) causing the diodes to generate continuous light radiation by applying a constant voltage differential across the diodes,
(c) concentrating and projecting the continuous light radiation on an area of the patient in registration with a musculoskeletal disorder,
(d) maintaining the continuous light radiation for a prescribed continuous treatment duration of up to approximately twenty minutes,
(e) causing the diodes to generate pulsed light radiation by applying a pulsed voltage differential across the diodes,
(f) concentrating and projecting the pulsed light radiation on the area of the patient in registration with the musculoskeletal disorder, and
(g) maintaining the pulsed light radiation for a prescribed pulsed treatment duration of up to approximately twenty minutes.

18. A method of treating musculoskeletal disorders in patients in accordance with claim 17 wherein a regimen of two combined treatments per day is applied.

19. A method of treating musculoskeletal disorders in patients in accordance with claim 17 wherein the prescribed continuous treatment duration is approximately between five and ten minutes and the prescribed pulse treatment duration is approximately between five and ten minutes.

20. A method of treating musculoskeletal disorders in patients in accordance with claim 17 wherein the continuous light radiation is concentrated and projected on an area of approximately 2 cm$^2$ and the pulsed light radiation is concentrated and projected on an area of approximately 2 cm$^2$.

21. A method of treating musculoskeletal disorders in patients in accordance with claim 17 wherein the continuous light radiation is concentrated and projected on the area with a light power density in the order of 20 mw/cm$^2$.

22. A method of treating musculoskeletal disorders in accordance with claim 17 wherein the pulsed light radiation is concentrated and projected on the area with an average light power of approximately 2.7 mw.

23. A method of treating musculoskeletal disorders in accordance with claim 17 wherein steps (e), (f) and (g) are performed prior to performing steps (b), (c) and (d).

24. A method of treating topical disorders including ulcers or wounds with red light radiation, the method comprising the steps of:
  (a) providing a plurality of light emitting diodes which generate noncoherent light radiation in a narrow bandwidth centered at approximately 660 nm,
  (b) causing the diodes to generate continuous light radiation by applying a constant voltage differential across the diodes,
  (c) concentrating and projecting the continuous light radiation on an area afflicted with a topical disorder,
  (d) maintaining the continuous light radiation for a prescribed continuous treatment duration of up to approximately twenty minutes,
  (e) causing the diodes to generate pulsed light radiation by applying a pulsed voltage differential across the diodes,
  (f) concentrating and projecting the pulsed light radiation on the area afflicted with said topical disorder, and
  (g) maintaining the pulsed light radiation for a prescribed pulsed treatment duration of up to approximately twenty minutes.

25. A method of treating topical disorder in patients in accordance with claim 24 wherein the continuous treatment duration is approximately 7 minutes and the pulsed treatment duration is approximately 7 minutes.

26. A method of treating a topical disorder in accordance with claim 24 wherein the prescribed continuous treatment duration is approximately between five and ten minutes and the prescribed pulsed treatment duration is approximately between five and ten minutes.

27. A method of treating a topical disorder in accordance with claim 24 wherein the continuous light radiation is concentrated and projected on an area of approximately 2 cm$^2$.

28. A method of treating a topical disorder in accordance with claim 24 wherein the continuous light radiation is concentrated and projected with a light power density of approximately 15 mw/cm$^2$.

29. A method of treating a topical disorder in accordance with claim 24 wherein the pulsed light radiation is concentrated and projected with an average light power of approximately 7.5 mw.

30. A method of treating a topical disorder in accordance with claim 24 wherein steps (e), (f) and (g) are performed prior to performing steps (b), (c) and (d).

* * * * *